US010328257B2

(12) United States Patent
Whitman et al.

(10) Patent No.: US 10,328,257 B2
(45) Date of Patent: Jun. 25, 2019

(54) ELECTRODE FIXATION IN INTERVENTIONAL MEDICAL SYSTEMS (71) Applicant: Medtronic, Inc., Minneapolis, MN (US)

(72) Inventors: Teresa A Whitman, Dayton, MN (US); Matthew D Bonner, Plymouth, MN (US); Jean M Carver, Blaine, MN (US); Raymond W Usher, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 15/336,284

(22) Filed: Oct. 27, 2016

(65) Prior Publication Data
US 2018/0117307 A1 May 3, 2018

(51) Int. Cl.
*A61N 1/05* (2006.01)
*A61B 17/34* (2006.01)
*A61N 1/375* (2006.01)
*A61N 1/362* (2006.01)

(52) U.S. Cl.
CPC .......... *A61N 1/059* (2013.01); *A61B 17/3468* (2013.01); *A61N 1/05* (2013.01); *A61N 1/37518* (2017.08); *A61N 1/362* (2013.01)

(58) Field of Classification Search
CPC ...... A61N 1/05; A61N 1/0539; A61N 1/0558; A61N 1/057; A61N 1/0573; A61N 1/0575; A61N 2001/0578; A61N 2001/058; A61N 2001/0587; A61N 2001/059; A61N 2001/0592; A61N 2001/0595
See application file for complete search history.

(56) References Cited

U.S. PATENT DOCUMENTS 3,814,104 A 6/1974 Irnich et al.
4,058,128 A * 11/1977 Frank .................. A61N 1/0587
607/130

(Continued)

OTHER PUBLICATIONS (PCT/US2017/058441) PCT Notification of Transmittal of the International Search Report and the Written Opinion of the International Searching Authority, dated Feb. 9, 2018, 13 pages.

(Continued)

*Primary Examiner* — Eugene T Wu (57) ABSTRACT

An implantable medical device assembly includes a mounting structure, an electrode, and fixation tines. The electrode protrudes from a surface of the structure, offset proximally from a distal end of the structure, and approximately centered between first and second sides of the structure. Each tine extends away from the surface—a first adjacent the first side, and a second adjacent the second side. Each tine is elastically deformable from a relaxed condition, in which the tine extends toward a proximal end of the structure, to an extended condition, in which the tine extends away from the distal end of the structure. A delivery tool has first and second longitudinally extending sidewalls to receive passage of the structure therebetween. When the structure distal end is located between proximal ends of the sidewalls, a rail-like edge of each sidewall receives, and elastically deforms to the extended condition, a corresponding tine.

15 Claims, 6 Drawing Sheets

(56) References Cited

U.S. PATENT DOCUMENTS

| | | | | |
|---|---|---|---|---|
| 4,066,085 A * | 1/1978 | Hess | | A61N 1/0587 607/131 |
| 4,103,690 A | 8/1978 | Harris | | |
| 4,136,702 A * | 1/1979 | Trabucco | | A61N 1/0587 607/130 |
| 4,142,530 A | 3/1979 | Wittkampf | | |
| 4,144,890 A | 3/1979 | Hess | | |
| 4,177,818 A * | 12/1979 | De Pedro | | A61N 1/0587 607/130 |
| 4,313,448 A * | 2/1982 | Stokes | | A61N 1/0587 607/130 |
| 4,357,946 A | 11/1982 | Dutcher et al. | | |
| 4,424,818 A * | 1/1984 | Doring | | A61N 1/0587 607/130 |
| 4,607,644 A | 8/1986 | Pohndorf | | |
| H356 H | 11/1987 | Stokes et al. | | |
| 5,050,600 A * | 9/1991 | Parks | | A61N 1/3625 607/10 |
| 5,300,107 A | 4/1994 | Stokes et al. | | |
| 5,423,879 A * | 6/1995 | Nyman | | A61N 1/05 607/122 |
| 5,443,492 A | 8/1995 | Stokes et al. | | |
| 5,545,207 A * | 8/1996 | Smits | | A61N 1/0587 607/130 |
| 5,571,162 A | 11/1996 | Lin | | |
| 5,871,532 A | 2/1999 | Schroeppel | | |
| 6,510,347 B2 | 1/2003 | Borkan | | |
| 7,085,606 B2 | 8/2006 | Flach et al. | | |
| 7,270,669 B1 | 9/2007 | Sra | | |
| 7,610,104 B2 | 10/2009 | Kaplan et al. | | |
| 7,647,109 B2 | 1/2010 | Hastings et al. | | |
| 7,771,838 B1 * | 8/2010 | He | | B23K 1/19 428/632 |
| 8,478,431 B2 | 7/2013 | Griswold et al. | | |
| 8,532,790 B2 | 9/2013 | Griswold | | |
| 2004/0176830 A1 * | 9/2004 | Fang | | A61N 1/0573 607/129 |
| 2004/0267343 A1 | 12/2004 | Flach et al. | | |
| 2006/0247753 A1 | 11/2006 | Wenger et al. | | |
| 2011/0251661 A1 | 10/2011 | Fifer et al. | | |
| 2011/0251662 A1 | 10/2011 | Griswold et al. | | |
| 2012/0172690 A1 | 7/2012 | Anderson et al. | | |
| 2012/0172892 A1 * | 7/2012 | Grubac | | A61N 1/3756 606/129 |
| 2013/0035748 A1 * | 2/2013 | Bonner | | A61N 1/056 623/1.11 |
| 2014/0207149 A1 | 7/2014 | Hastings et al. | | |
| 2015/0051682 A1 | 2/2015 | Schmidt et al. | | |
| 2016/0121102 A1 | 5/2016 | Tockman et al. | | |
| 2018/0071543 A1 * | 3/2018 | Taff | | A61N 1/37512 |
| 2018/0099138 A1 * | 4/2018 | Bonner | | A61B 17/3468 |

OTHER PUBLICATIONS www.mana-tech.com/factsheets/HomerMammalok.pdf, Anglotech (PBN Medicals Denmark A/S), 1 page.

U.S. Appl. No. 15/287,122, filed Oct. 6, 2016, 28 pages.

* cited by examiner

ELECTRODE FIXATION IN INTERVENTIONAL MEDICAL SYSTEMS

CROSS-REFERENCE TO RELATED APPLICATION

The instant application is related to the co-pending and commonly assigned United States patent application entitled, ELECTRODE FIXATION IN INTERVENTIONAL MEDICAL SYSTEMS, having the Ser. No. 15/287,122, which was filed on Oct. 6, 2016, and is hereby incorporated by reference.

TECHNICAL FIELD

The present invention pertains to interventional medical systems, and, more specifically, to implantable electrode fixation at a stimulation site.

BACKGROUND

Figure 1:
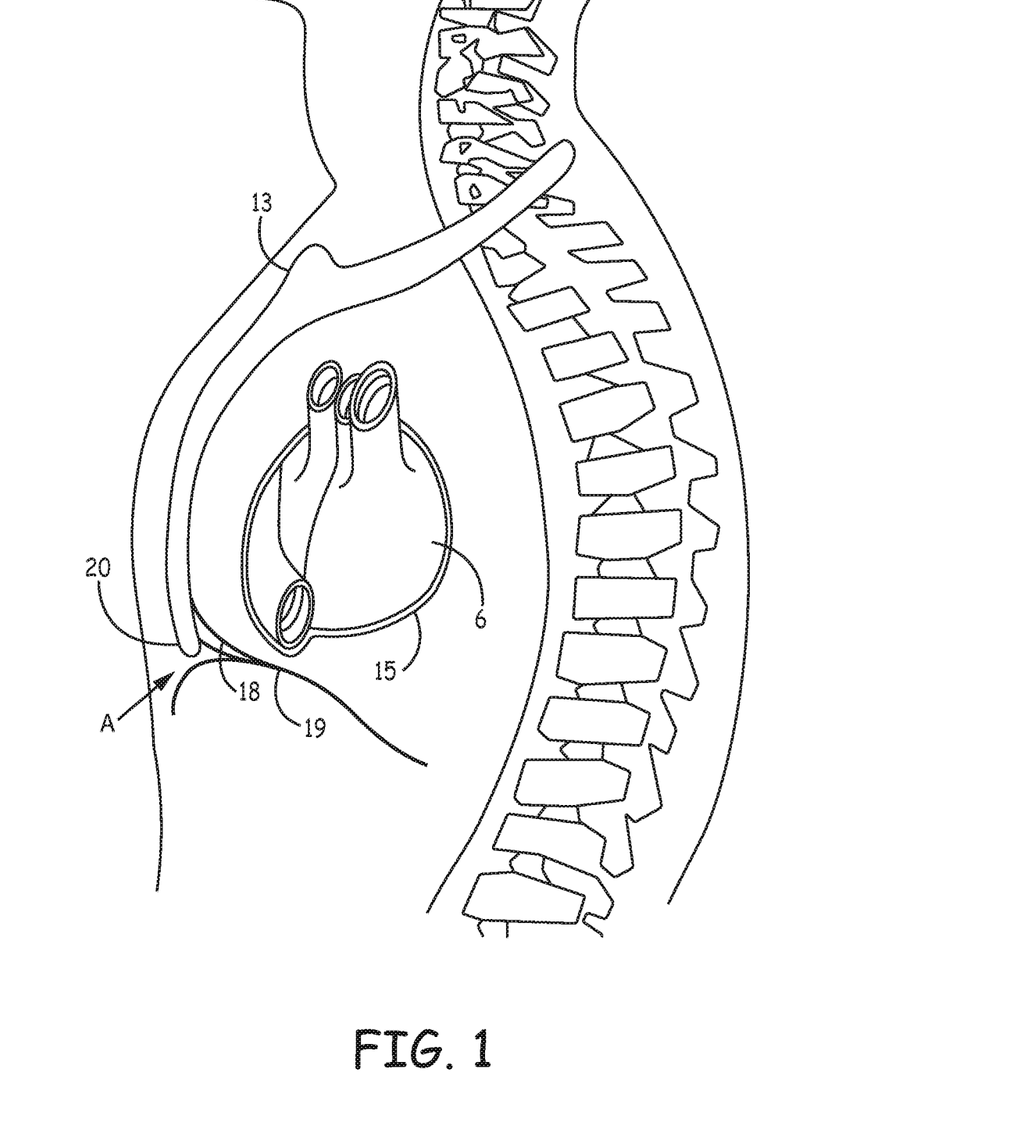
FIG. 1 is a schematic depicting a sub-sternal access site through which an implantable electrode may be passed for securing to an epicardial surface of a patient's heart.

An implantable medical device, for the delivery of stimulation therapy, may include an electrode and a fixation component configured to hold the electrode in intimate contact with tissue at a stimulation site. One type of such a device may be an implantable cardiac pacemaker that includes a pulse generator and a pacing electrode coupled to the generator, for example, by an elongate insulated lead wire. A pacing site may be located on an epicardial surface of the heart, for example, on the left side of the heart for the application of pacing therapy to treat heart failure. FIG. 1 is a schematic showing an access site A for creating a passageway between a patient's diaphragm 19 and xiphoid process 20 of sternum 13, for example, to implant a pacing electrode on an epicardial surface 6 of the patient's heart, which is enclosed within the pericardial sac 15. After making a superficial incision, an operator may open a passageway between diaphragmatic attachments 18 and diaphragm 19 by using blunt dissection tools and techniques that are known in the art. Then, the operator may employ a piercing tool to pass a guide wire through the pericardial sac 15, also according to methods known in the art. The operator may use fluoroscopic guidance to position a distal portion of the guide wire along a portion of epicardial surface 6, at which a target site is located, and then pass a guiding sheath over the positioned guide wire. The guiding sheath then serves as a conduit for delivery of the implantable electrode to the target site. In this context, to deliver and then fix, or secure the implantable electrode at an epicardial site, there is a need for new configurations of interventional systems and associated implantable device assemblies.

SUMMARY

An implantable medical device assembly, according to some embodiments, includes a mounting structure, an electrode, and first and second tissue-penetrating fixation tines; wherein the electrode protrudes from a surface of the structure at a location that is offset proximally from a distal end of the structure and is approximately centered between first and second sides of the structure, and wherein a segment of each fixation tine extends away from the surface of the structure, the first fixation tine segment, at a location adjacent the first side and distal end of the structure, and the second fixation tine segment, at a location adjacent the second side and distal end of the structure. Each tine segment is elastically deformable from a relaxed condition to an extended condition; wherein, in the relaxed condition, each tine extends toward a proximal end of the mounting structure so that a piercing tip of each tine is located adjacent to the electrode, and, in the extended condition, each tine extends away from the distal end of the mounting structure, so that each piercing tip is located distal to the distal end of the mounting structure.

In some embodiments, each fixation tine is a component formed from a super-elastic wire, and the component may include a mounting segment (e.g., pre-formed in an L-shape), and the above-described segment (e.g., pre-formed in a V-shape), which extends from the surface of the mounting structure and is terminated by the piercing tip. The segments may bend toward one another, in a single plane, the same for both. In the above described assembly, the mounting structure may include first and second channels that extend lengthwise, between the proximal and distal ends of the structure, wherein the mounting segment of each fixation tine extends a corresponding channel.

An interventional medical system, according to some embodiments, includes the above described device assembly and a delivery tool, which has first and second longitudinally extending sidewalls spaced apart from one another to receive passage of the assembly mounting structure therebetween, so that, when the structure is passed therebetween, until the distal end thereof is located between proximal ends of the sidewalls, a rail-like edge of each sidewall receives in engagement therewith, and elastically deforms to the extended condition, a corresponding fixation tine segment. According to some methods, after an operator positions the holding member and the device assembly, with the fixation tines in the extended condition, at an epicardial site, the operator releases the fixation tines from the extended condition, to engage with tissue at the site, by applying a push force to the mounting structure of the device assembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
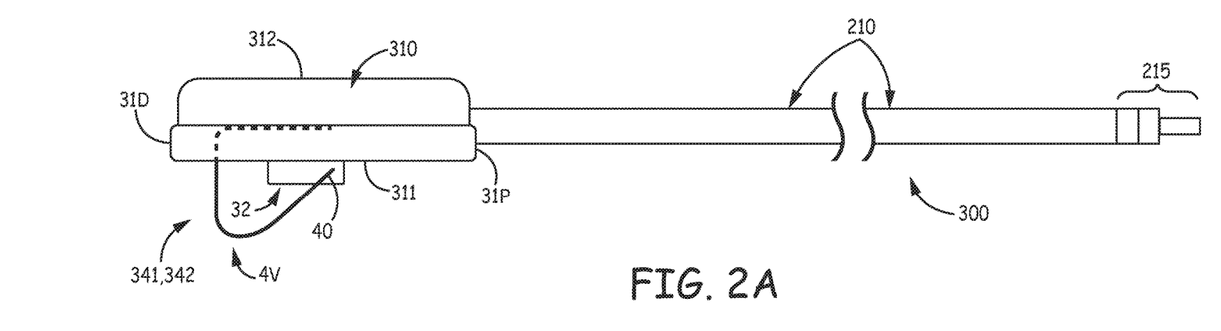
FIGS. 2A-C are various plan views of an implantable medical device assembly, according to some embodiments.
Figures 2B, 2C:
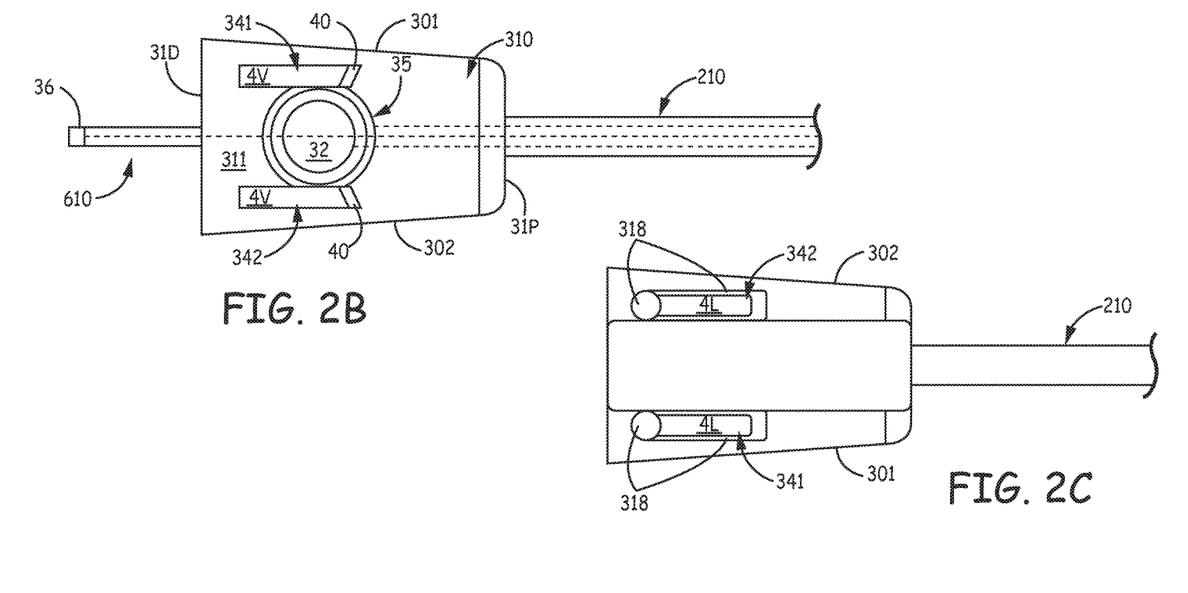

FIGS. 2A-B are plan views, from different perspectives, of an implantable medical device assembly 300, according to some embodiments. A mounting structure 310 of device assembly 300 is shown having a length defined from a proximal end 31P to a distal end 31D thereof, a thickness defined from a first surface 311 to a second surface 312 thereof, and a width defined from a first side 301 to a second side 302 thereof. FIGS. 2A-B illustrate assembly 300 including an electrode 32 protruding from first surface 311 of structure 310 at a location offset proximally from structure distal end 31D and offset from and approximately centered between first and second sides 301, 302. According to some exemplary embodiments, structure 310 may be formed from a biocompatible and biostable insulative polymer, such as silicone, or urethane, or a combination thereof. FIGS. 2A-B further illustrate first and second tissue-penetrating fixation tines 341, 342 of assembly 300 being located on either side of electrode 32, wherein first tine 341 extends from surface 311 of structure 310 at a location adjacent to first side 301 and distal end 31D, and second tine 342 extends from surface 311 at a location adjacent to second side 302 and distal end 31D. Each tine 341, 342 includes a tissue-piercing tip 40, and FIGS. 2A-B show tines 341, 342 in a relaxed condition, bending toward proximal end 31P and first surface 311 of structure 310, so that each piercing tip 40 is located adjacent to electrode 32. According to preferred embodiments, each tine 341, 342 is formed from a superelastic material and includes a pre-formed V-shaped segment 4V configured to secure electrode 32, in intimate tissue contact, at a stimulation site on an epicardial surface of a patient's heart. Electrode 32 may be constructed from any suitable material and by any suitable method known to those skilled in the art of medical electrical cardiac pacing.

Pre-formed V-shaped segment 4V of each fixation tine 341, 342 is elastically deformable from the illustrated relaxed condition, which is that of the pre-formed V-shape, to an extended condition, in which each segment 4V extends distally away from distal end 31D of structure 310, so that tips 40 are located distal to structure distal end 31D, for example, as described below in conjunction with FIG. 4A. Tines 341, 342 may be held in the extended condition until an operator positions assembly 300 in proximity to a stimulation site, after which the operator may release tines 341, 342 from the extended condition so that piercing tips 40 'bite', or penetrate into tissue adjacent the site, thereby securing electrode 32 in intimate tissue contact for stimulation therapy.

With reference to FIG. 2A, in conjunction with FIG. 2C, which is another plan view of device assembly 300, each tine 341, 342 may be secured to structure 310 by a pre-formed L-shaped segment 4L thereof (dashed lines in FIG. 2A). FIG. 2C illustrates each L-shaped segment extending in a corresponding channel 318 of mounting structure, being interlocked therewith, and, for example, further secured thereto by a backfill of a medical grade adhesive material, according to some embodiments. According to the illustrated embodiment, each channel 318 extends through structure 310, from first surface 311 toward second surface 312 and then lengthwise adjacent to a corresponding side 301, 302 of structure 310. However, according to alternate embodiments, in which the means for mounting tines 341, 342 is varied, what is herein designated as the L-shaped segment 4L of the illustrated embodiment can be pre-formed into any other suitable shape that conforms to alternate mounting means.

Figures 3A, 3B:
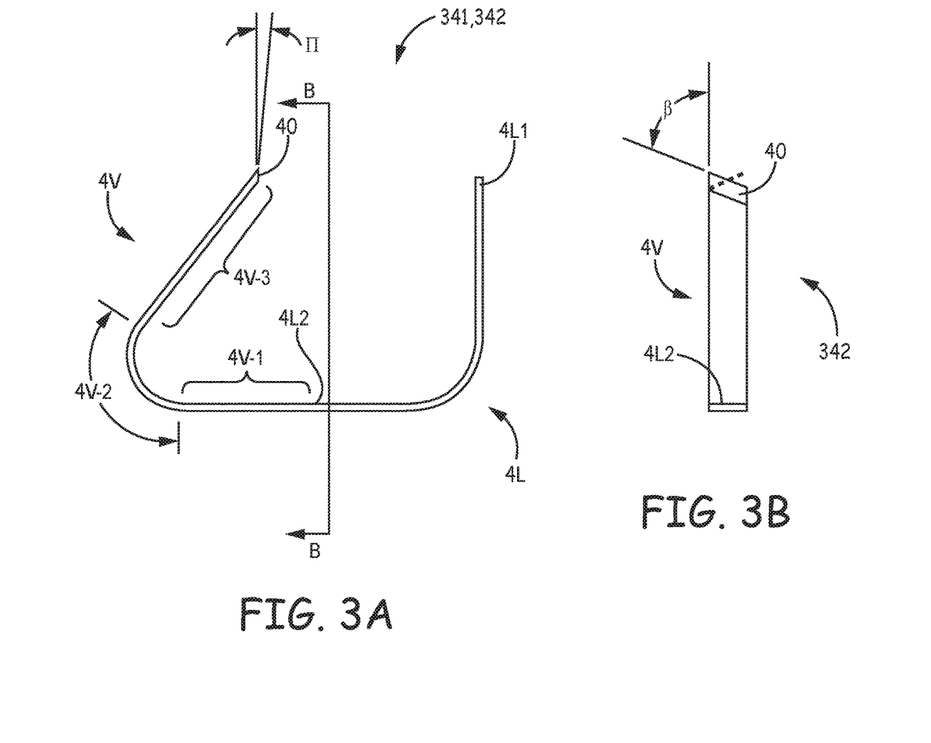
FIGS. 3A-B are a plan view and a cross-section view of a tissue-penetrating tine component, according to some embodiments.

FIG. 3A is a plan view of either of tissue-penetrating fixation tines 341, 342 as a separate component from assembly 300, according to some embodiments. FIG. 3A illustrates tine 341, 342 including the aforementioned pre-formed L-shaped and V-shaped segments 4L, 4V, wherein L-shaped segment 4L extends from a first end 4L1 thereof to a second end 4L2 thereof around a bend that encloses a 90 degree angle, and V-shaped segment 4V extends from second end 4L2 of L-shaped segment 4L to piercing tip 40, and bends toward L-shaped segment 4L. FIG. 3A further illustrates V-shaped segment 4V including a first, relatively straight, portion 4V-1, a second, arched, portion 4V-2, and a third, relatively straight, portion 4V-3, wherein second portion 4V-2 connects first and third portions 4V-1, 4V-3, and third portion 4V-3 is terminated by piercing tip 40. A length of third portion 4V-3, for example, about 0.12 inch, sets a depth to which each tine 341, 342 can penetrate into tissue at an implant site; and a length of second portion 4V-2, for example, about 0.08 inch around a radius of about 0.03 inch, adds a bit of depth to the penetration and determines how much tissue is encompassed by the penetrating tines 341, 342. The release of tines 341, 342 for 'biting' is described in greater detail below, in conjunction with FIG. 6.

FIG. 3B is cross-section view of tine 342, through section line B-B of FIG. 3A, and, with reference to FIG. 3B in conjunction with FIG. 3A, each tine component 341, 342 has a generally rectangular axial cross-section that is uniform along both segments 4L, 4V, sans piercing tip 40, wherein a single plane in which both segments 4L, 4V bend is orthogonal to longer sides of the axial cross-section. According to an exemplary embodiment, tine components 341, 342 may be formed from a rolled Nitinol wire (e.g., having a diameter of approximately 0.012 inch, prior to rolling), and piercing tip 40 is formed by a first angled surface cut in one of the longer sides of the axial cross-section, according to an angle π (FIG. 3A), for example, of about 25 degrees. Each of tine components may also include a second angled surface cut into one of the shorter sides of the axial cross-section, according to an angle β (FIG. 3B), for example, of about 60 degrees, wherein, with further reference to FIG. 3B, in conjunction with FIG. 2B, the second angled surfaces of tines 341, 342 face generally toward one another in assembly 300, such that the dashed line in FIG. 3B represents the second angled surface of tine 341.

With further reference to FIGS. 2A-B, when device assembly 300 forms an implantable medical electrical lead, assembly 300 further includes an elongate conductor that is coupled to electrode 32 (dashed line in FIG. 2B), and an elongate insulation body 210 that is joined to mounting structure 310 and extends around the conductor to provide electrical isolation. According to the illustrated embodiment, the conductor extends proximally from proximal end 31P of structure 310 and within insulation body 210 to a connector subassembly 215, which is configured for coupling to an implantable pulse generator, such as a pacemaker (not shown). FIG. 2B further illustrates device assembly including one or more optional additional electrodes 35, 36 and corresponding insulated conductors (dashed lines) coupled thereto. Optional electrode 35 is shown mounted to surface 311 of structure 310, for example, for bipolar function with electrode 32, according to some embodiments; alternately, electrode 35 can be mounted opposite electrode 32, to second surface 312 of mounting structure 310. Optional electrode 36 is shown mounted to an elongate insulation body 610 that extends distally from distal end 31D of mounting structure 310, and through which the corresponding conductor (dashed line) extends. According to an exemplary embodiment that includes electrode 36, electrode 36 may be spaced apart from electrode 32 by a distance of about one to two inches, for example, to create a 'wide' dipole for atrial sensing. A construction of the conductor(s), insulation body 210 (and optional body 610), and connector subassembly 215 of assembly 300, as well as of the pulse generator, may be according to any suitable means known to those skilled in the art of implantable medical stimulation systems.

Figures 4A, 4B, 4C:
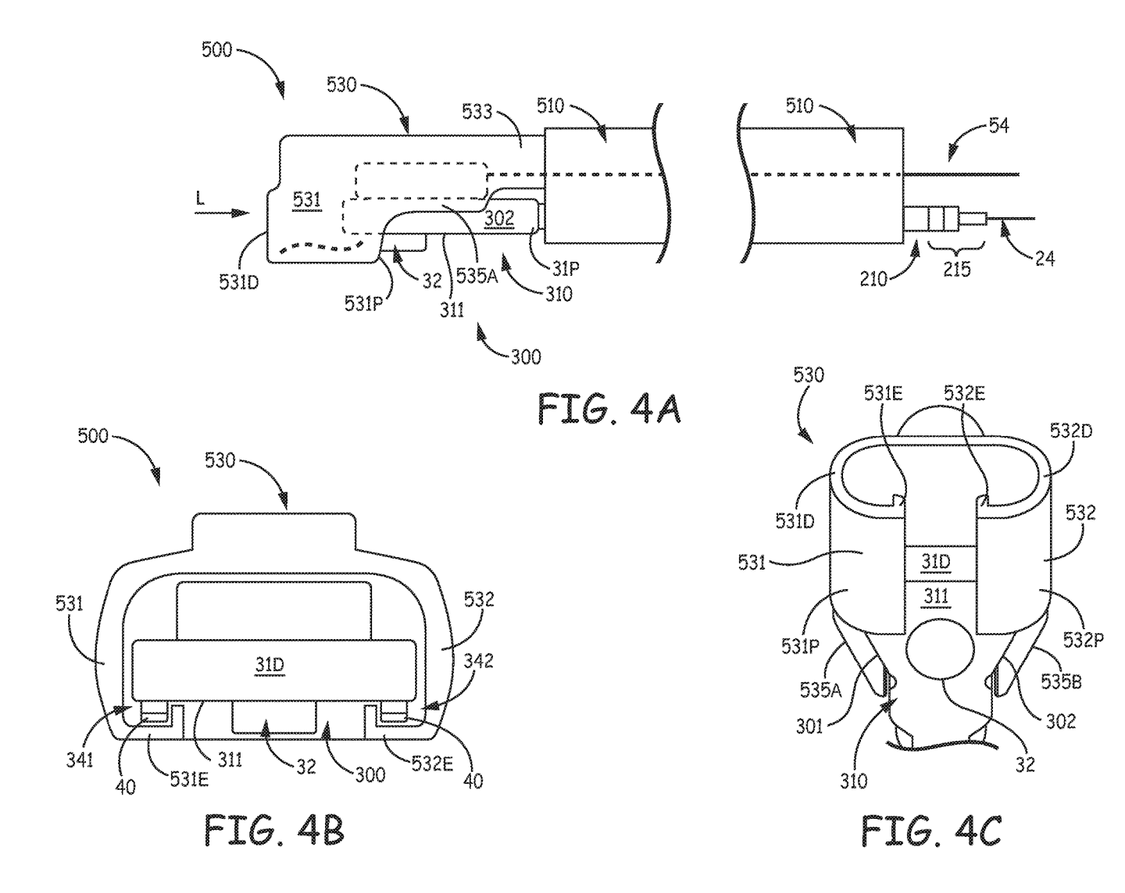
FIG. 4A is a plan view of an interventional medical system, according to some embodiments, that includes a delivery tool together with the device assembly of FIGS. 2A-C.
FIG. 4B is an end view of the system, according to some embodiments.
FIG. 4C is a perspective view of a portion of the system, according to some embodiments.

FIGS. 4A-B are a plan view and an end view of an interventional medical system, according to some embodiments, that includes a delivery tool 500 together with device assembly 300; and FIG. 4C is perspective view of a portion of the system, according to some embodiments. FIGS. 4A-C illustrate device assembly 300 received between first and second longitudinally extending sidewalls 531, 532 of a holding member 530 of delivery tool 500, which holding member 530 is attached to a distal end of an elongate shaft 510 of tool 500. FIGS. 4B-C illustrate sidewalls 531, 532 being spaced apart from one another, to receive passage of device assembly 300 therebetween, and each sidewall 531, 532 including a rail-like edge 531E, 532E. With further reference to FIGS. 4A and 4C, each sidewall 531, 532 extends over a length defined from a proximal end 531P, 532P thereof to a distal end 531D, 532D thereof, and edges 531E, 532E extend along the length. According to the illustrated embodiment, each sidewall edge 531E, 532E is sized to receive in engagement therewith, and to elastically deform, from the relaxed condition to the extended condition, V-shaped segment 4V of a corresponding fixation tine 341, 342, when proximal end 31P of device assembly mounting structure 310, with surface 311 facing toward edges 531E, 532E, is passed between sidewalls 531, 531 (e.g., per arrow L), from distal ends 531D, 532D thereof to proximal ends 531P, 532P thereof, and then proximally beyond. (Dashed lines in FIG. 4A depict distal end 31D of mounting structure 310 between holding member sidewalls 351, 352, and the extended condition of tines 341, 342, being engaged in edges 351E, 352E.) Thus, an operator may employ tool 500 to position device assembly 300, with tines 341, 342 in the extended position, at an epicardial site.

According to some embodiments, holding member 530 further includes means for engaging device assembly mounting structure 310, in proximity to proximal end 31P, when distal end 31D is located between holding member sidewalls 531, 532, to prevent distal end 31D from passing proximally out from between sidewalls 531, 532. FIGS. 4A and 4C illustrate this means being first and second stop members 535A, 535B that extend proximally from respective sidewall proximal ends 531P, 532P, and are oriented to abut respective first and second sides 301, 302 of mounting structure 310, for example, by extending inward toward one another, as best seen in FIG. 4C. Furthermore, with reference to FIGS. 2B-C, in conjunction with FIG. 4C, mounting structure sides 301, 302 may taper toward one another so that the width of structure 310 in proximity to proximal end 31P is less than the width in proximity to distal end 31D.

According to some embodiments, shaft 510 of tool 500 is formed by a tubular member, for example, which is attached around a shank 533 of holding member 530, as shown in FIG. 4A. FIG. 4A further illustrates insulation body 210 of device assembly 300 extending within shaft 510 of tool 500 so that connector assembly 215 extends proximally therefrom. But, in some alternate embodiments, insulation body 210 may extend alongside delivery tool shaft 510.

According to an exemplary embodiment, shaft 510 of delivery tool 500, for example, extending over a length of approximately 30 cm to 35 cm, may be formed by a stainless steel braid-reinforced medical grade polymer of one or more appropriate grades of polyether block amide (e.g., PEBAX® 6333 and 7033); and holding member 530 of tool 500 may be formed from an appropriate grade of polyether block amide (e.g., PEBAX® 7233) and include a radiopaque marker bonded thereto, for example, a Platinum/Iridium or gold marker, or a polyamide material with a radiopaque filler, such as Tungsten-filled Vestamid®.

Figure 5:
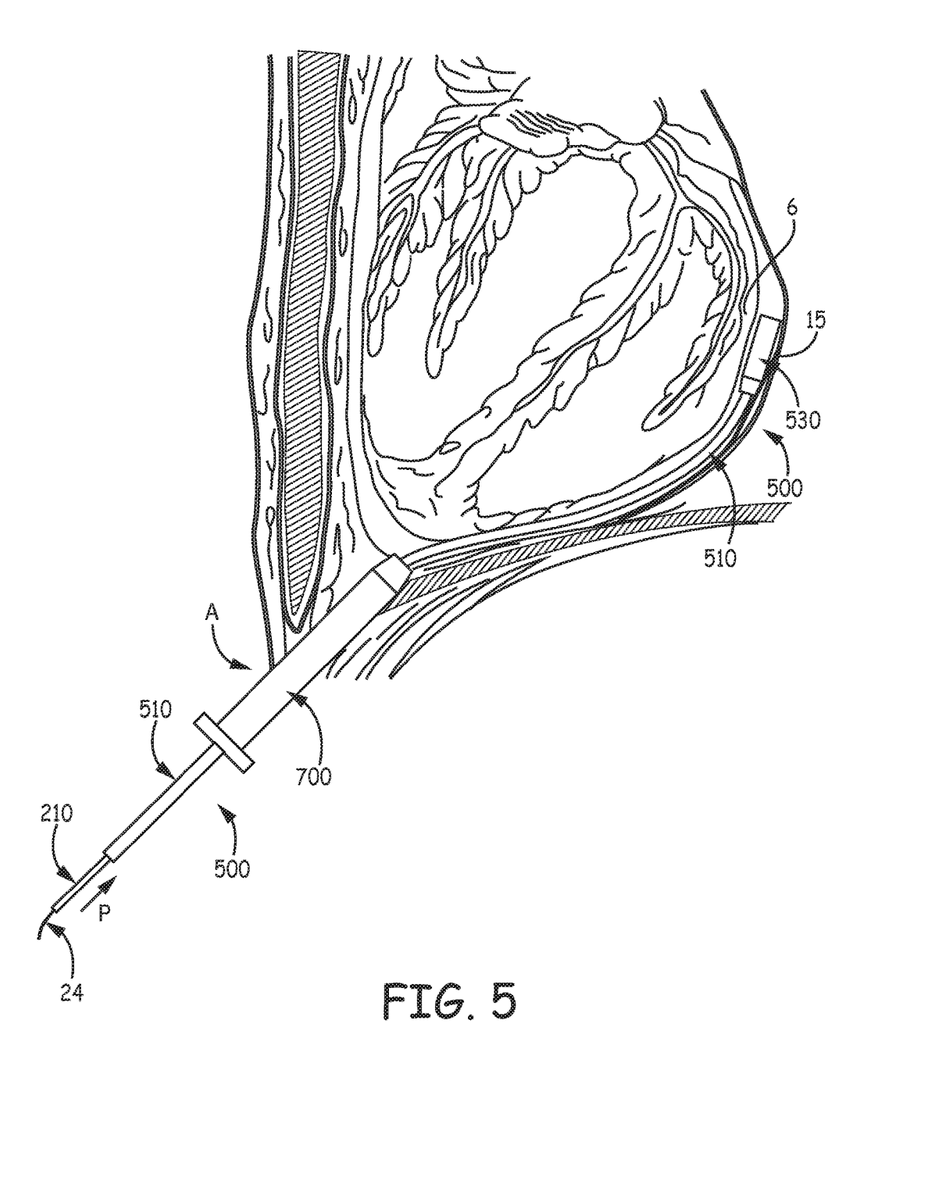
FIG. 5 is a schematic showing the delivery tool positioned for securing an electrode of the medical device assembly at an epicardial site, according to some methods.

FIG. 5 is a schematic showing holding member 530 of delivery tool 500 having been positioned in the pericardial space, via sub-xiphoid access, so the operator can secure electrode 32 of device assembly 300 at the epicardial site, for example, to provide pacing stimulation. FIG. 5 illustrates a guiding sheath 700 providing a passageway for the insertion of delivery tool 500 into the pericardial space, between epicardial surface 6 and pericardial sac 15, through access site A, which may be formed by any suitable method known in the art, for example, as described above in conjunction with FIG. 1. Fluoroscopic or video monitoring may be employed for guidance in positioning holding member 530. Alternately, the operator may gain access to the pericardial space, to position holding member 530 and assembly 300, via a thoracotomy by methods known in the art. According to some methods, after positioning holding member 530 and device assembly 300 at the epicardial site, the operator applies a push force to mounting structure 310 through an elongate stiffener 24 that extends in sliding engagement within insulation body 210 of device assembly 300, per arrow P, thereby moving device assembly 300 distally relative to delivery tool holding member 530 and releasing fixation tines 341, 342 to penetrate into tissue at the epicardial site. Then, the operator can retract tool 500 from the pericardial space and withdraw stiffener 24 from device assembly 300. According to some alternate embodiments and methods, and with reference back to FIG. 4A, the operator can apply the push force to mounting structure 310 through an optional ejector rod 54 of the interventional medical system, which extends in sliding engagement within tool shaft 510.

Figure 6:
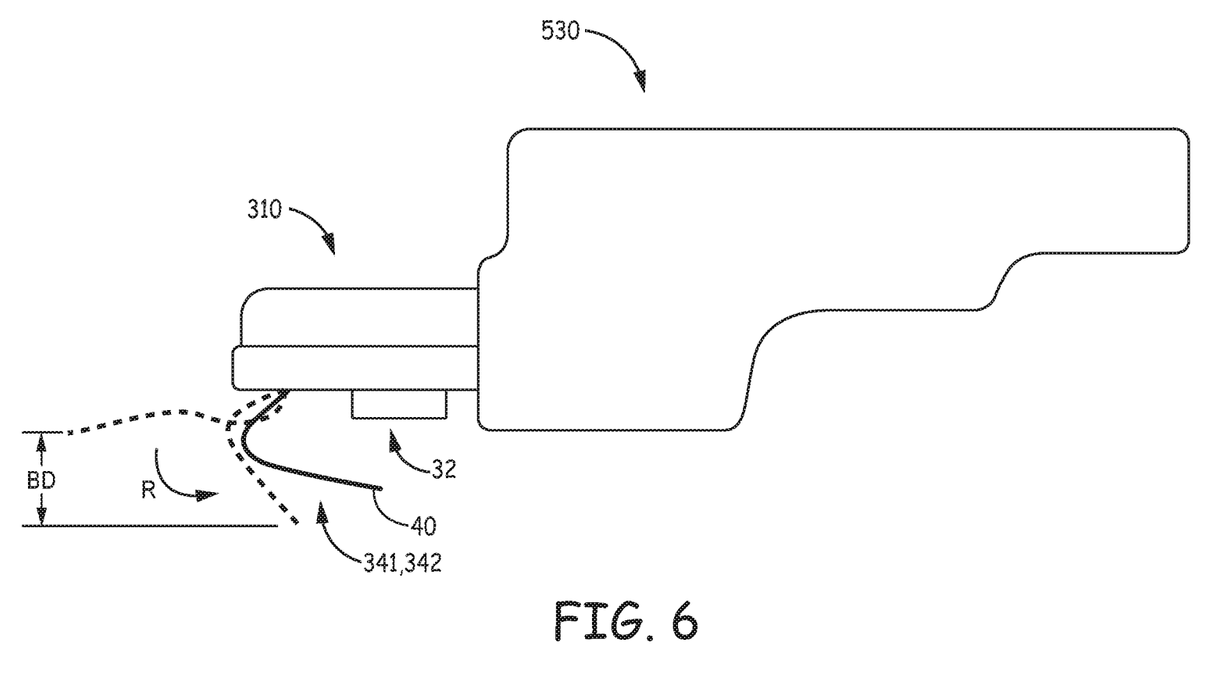
FIG. 6 is a schematic depicting release of tissue-penetrating fixation tines in the interventional medical system, according to some embodiments.

FIG. 6 is a schematic depicting the release of fixation tines 341, according to some embodiments. In FIG. 6, positions of tines 341, 342, which are illustrated with dashed-line representations, correspond to a trajectory of tine release, per arrow R, for penetration of tine piercing tips 40 into tissue. The solid line representation of tines 341, 342 generally corresponds to full engagement thereof with tissue, which secures electrode 32 to the epicardial stimulation site. An approximate penetration depth BD of tines 341, 342 may be about 0.132 inch (3.3 mm), as dictated by the above disclosed exemplary radius and lengths of tine portions 4V-2 and 4V-3 (FIG. 3A).

In the foregoing detailed description, the invention has been described with reference to specific embodiments. However, it may be appreciated that various modifications and changes can be made without departing from the scope of the invention as set forth in the appended claims.

The invention claimed is:

1. An implantable medical device assembly comprising:
   a mounting structure having a length defined from a proximal end thereof to a distal end thereof, a width defined from a first side thereof to a second side thereof, and a surface that extends along the length and across the width;
   an electrode protruding from the surface of the mounting structure at a location offset proximally from the distal end of the structure, and offset from and approximately centered between the first and second sides of the structure; and
   first and second tissue-penetrating fixation tines located on either side of the electrode, each tine including a pre-formed V-shaped segment that extends away from the surface of the mounting structure, the segment of the first tine extending from the surface at a location adjacent to both the first side and the distal end of the structure, the segment of the second tine extending from the surface at a location adjacent to both the second side and the distal end of the structure, each segment including a piercing tip, and each segment being elastically deformable from a relaxed condition to an extended condition, the relaxed condition being that of the pre-formed V-shape, in which each segment extends toward the proximal end and the surface of the mounting structure so that each piercing tip is located adjacent to the electrode, and the extended condition being that in which each segment extends distally away from the distal end of the mounting structure so that each piercing tip is located distal to the distal end of the structure.

2. The assembly of claim 1, wherein:
   the mounting structure further comprises first and second channels extending lengthwise, the first channel being located adjacent to the first side of the structure and the second channel being located adjacent to the second side of the structure; and
   each fixation tine further includes another segment extending in a corresponding channel of the first and second channels of the mounting structure.

3. The assembly of claim 2, wherein the other segment of each fixation tine comprises an L-shaped segment.

4. The assembly of claim 1, further comprising another electrode mounted to mounting structure for bipolar function with the electrode that protrudes from the surface of the mounting structure.

5. The assembly of claim 1, further comprising:
   an elongate insulation body joined to the mounting structure and extending distally therefrom;
   another electrode mounted to the elongate insulation body; and
   an elongate conductor coupled to the electrode and extending therefrom within the insulation body.

6. The assembly of claim 2, wherein:
   each fixation tine has a generally rectangular axial cross-section, the axial cross-section being uniform along the both segments of the tine, except for the piercing tips, and longer sides of each axial cross-section being orthogonal to a single plane in which both segments of each tine bend; and
   each fixation tine is oriented so that one of the longer sides of the axial cross section thereof faces generally toward the surface of the mounting structure, when the pre-formed V-shaped segment is in the relaxed condition, and faces generally away from the surface of the mounting structure, when the pre-formed V-shaped segment is deformed into the extended condition.

7. The assembly of claim 6, wherein the piercing tip of each fixation tine includes an angled surface, the angled surfaces facing generally toward one another.

8. The assembly of claim 1, wherein the first and second sides of the mounting structure taper toward one another so that the width of the structure in proximity to the proximal end of the structure is less than the width of the structure in proximity to the distal end of the structure.

9. The assembly of claim 1, further comprising:
   an elongate conductor coupled to the electrode and extending therefrom within the mounting structure to the proximal end thereof and proximally therefrom; and
   an elongate insulation body joined to the mounting structure and extending proximally therefrom, the body extending around the conductor to provide electrical isolation thereof.

10. An interventional medical system comprising:
    an implantable medical device assembly comprising:
       a mounting structure having a length defined from a proximal end thereof to a distal end thereof, a width defined from a first side thereof to a second side thereof, and a surface that extends along the length and across the width;
       an electrode protruding from the surface of the mounting structure at a location offset proximally from the distal end of the structure, and offset from and approximately centered between the first and second sides of the structure; and
       first and second tissue-penetrating fixation tines located on either side of the electrode, each tine including a pre-formed V-shaped segment that extends away from the surface of the mounting structure, the segment of the first tine extending from the surface at a location adjacent to both the first side and the distal end of the structure, the segment of the second tine extending from the surface at a location adjacent to both the second side and the distal end of the structure, each segment including a piercing tip, and each segment being elastically deformable from a relaxed condition to an extended condition, the relaxed condition being that of the pre-formed V-shape, in which each segment extends toward the proximal end and the surface of the mounting structure so that each piercing tip is located adjacent to the electrode, and the extended condition being that in which each segment extends distally away from the distal end of the mounting structure so that each piercing tip is located distal to the distal end of the structure;
    a delivery tool comprising:
       an elongate shaft extending from a proximal end thereof to a distal end thereof; and
       a holding member attached to the distal end of the shaft, the holding member including first and second longitudinally extending sidewalls spaced apart from one another to receive passage of the device assembly mounting structure therebetween, each sidewall extending over a length defined from a proximal end thereof to a distal end thereof, and each sidewall including a rail-like edge extending along the length, each rail-like edge being sized to receive in engagement therewith, and to elastically deform the segment of a corresponding fixation tine from the relaxed condition to the extended condition, when the proximal end of the mounting structure, with the surface of the mounting structure facing toward the rail-like edges, is passed between the holding member sidewalls of the tool, from the distal ends of the sidewalls to the proximal ends of the sidewalls and proximally beyond; and means for applying a push force to the mounting structure, when the distal end of the structure is located between the holding member sidewalls of the delivery tool.

11. The system of claim 10, wherein the delivery tool holding member further comprises means for engaging the device assembly mounting structure in proximity to the proximal end thereof, when the distal end of the structure is located between the holding member sidewalls, to prevent the distal end of the mounting structure from passing proximally out from between the holding member sidewalls.

12. The system of claim 11, wherein the means for engaging the device assembly mounting structure in proximity to the proximal end thereof comprises a first stop member extending proximally from the proximal end of the first sidewall and a second stop member extending proximally from the proximal end of the second sidewall, the first and second stop members being oriented to abut the first and second sides of the device assembly mounting structure, when the distal end of the structure is located between the holding member sidewalls.

13. The system of claim 10, wherein the implantable medical device assembly further comprises:

an elongate conductor coupled to the electrode and extending therefrom within the mounting structure to the proximal end thereof and proximally therefrom; and an elongate insulation body joined to the mounting structure and extending proximally therefrom, the body extending around the conductor to provide electrical isolation thereof.

14. The system of claim 13, wherein the means for applying the push force comprises an elongate stiffener sized to fit in sliding engagement within the insulation body.

15. The system of claim 10, wherein the means for applying the push force comprises an ejector rod that extends in sliding engagement within the elongate shaft of the delivery tool.

* * * * *